United States Patent
Tsai et al.

(10) Patent No.: US 8,309,348 B2
(45) Date of Patent: *Nov. 13, 2012

(54) SYNGAS CONVERSION METHOD USING ASYMMETRIC MEMBRANE AND ANAEROBIC MICROORGANISM

(75) Inventors: Shih-Perng Tsai, Naperville, IL (US); Rathin Datta, Chicago, IL (US); Rahul Basu, St. Charles, IL (US); Seong-Hoon Yoon, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/240,848

(22) Filed: Sep. 22, 2011

(65) Prior Publication Data
US 2012/0009638 A1    Jan. 12, 2012

Related U.S. Application Data

(63) Continuation-in-part of application No. 12/036,007, filed on Feb. 22, 2008.

(51) Int. Cl.
C12P 7/06 (2006.01)
C12P 7/52 (2006.01)
C12P 7/54 (2006.01)
C12P 7/16 (2006.01)
C12P 7/04 (2006.01)

(52) U.S. Cl. .......... 435/297.2; 435/297.1; 435/401; 435/140; 435/141; 435/157; 435/161; 435/160

(58) Field of Classification Search .......... 435/297.1, 435/297.2, 401, 140, 141, 157, 161, 160
See application file for complete search history.

(56) References Cited

U.S. PATENT DOCUMENTS
4,266,026 A * 5/1981 Breslau .......... 435/99
2007/0275447 A1 * 11/2007 Lewis et al. .......... 435/161

FOREIGN PATENT DOCUMENTS
WO    WO9002170    * 3/1990
* cited by examiner

*Primary Examiner* — William H Beisner
*Assistant Examiner* — Danielle Henkel (57) ABSTRACT

A stable method for producing liquid products such as ethanol, propanol, butanol and other chemicals from syngas components that contacts CO or a mixture of $CO_2$ and $H_2$ with a highly porous side of an asymmetric membrane under anaerobic conditions and transfers these components into contact with microorganisms contained within bio-pores of the membrane. A liquid contacting side of the membrane utilizes a dense layer to control hydration of the bio-pores with a liquid phase. The gas feed directly contacts the microorganisms in the bio-pores and maximizes their utilization of the syngas. Metabolic products produced by the microorganisms leave the membrane through the side opposite the entering syngas. This method establishes a unitary direction across the membrane for the supply of the primary feed source to the microorganisms and the withdrawal of metabolically produced products. The feed and product flow improves productivity and performance of the microorganism and the membrane.

21 Claims, 5 Drawing Sheets

SYNGAS CONVERSION METHOD USING ASYMMETRIC MEMBRANE AND ANAEROBIC MICROORGANISM

CROSS REFERENCE TO RELATED APPLICATION

This application is a continuation-in-part of application Ser. No. 12/036,007, filed on Feb. 22, 2008 and entitled SYNGAS CONVERSION SYSTEM USING ASYMMETRIC MEMBRANE AND ANAEROBIC MICROORGANISM claims priority therefrom, and incorporates the teachings thereof herein by reference.

BACKGROUND

1. Field of the Invention

This invention relates to the biological conversion of CO and mixtures of $CO_2$ and $H_2$ to liquid products.

2. Detailed Description

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers).

For example, breaking down these recalcitrant structures to provide fermentable sugars for bioconversion to ethanol typically requires pretreatment steps together with chemical/enzymatic hydrolysis. Furthermore, conventional yeasts are unable to ferment the $C_5$ sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, n-butanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas can be made from many other carbonaceous feedstocks such as natural gas, reformed gas, peat, petroleum coke, coal, solid waste and land fill gas, making this a more universal technology path.

However, this technology path requires that the syngas components CO and $H_2$ be efficiently and economically dissolved in the aqueous medium and transferred to anaerobic microorganisms that convert them to the desired products. And very large quantities of these gases are required. For example, the theoretical equations for CO or $H_2$ to ethanol are:

Thus, 6 moles of relatively insoluble gases such as CO or $H_2$ have to transfer to an aqueous medium for each mole of ethanol. Other products such as acetic acid and n-butanol have similar large stoichiometric requirements for the gases. Furthermore, the anaerobic microorganisms that bring about these bioconversions generate very little metabolic energy from these bioconversions. Consequently they grow very slowly and often continue the conversions during the non-growth phase of their life cycle to gain metabolic energy for their maintenance. To get high yields and production rates the cell concentrations in the bioreactor need to be high and this requires some form of cell recycle or retention.

Cell retention by formation of biofilms is a very good and often inexpensive way to increase the density of microorganisms in bioreactors. This requires a solid matrix with large surface area for the microorganisms to colonize and form a biofilm that contains the metabolizing microorganisms in a matrix of biopolymers that the microorganisms generate. Trickle bed and some fluidized bed bioreactors make use of biofilms to retain microorganisms on solid surfaces while providing dissolved gases in the liquid by flow past the solid matrix. They suffer from either being very large or unable to provide sufficient gas dissolution rates.

Particular forms of membranes have found use in supporting specific types of microorganisms for waste water treatment processes. U.S. Pat. No. 4,181,604 discloses the use of hollow fiber membranes for waste treatment where the outer surface of the fibers supports a layer of microorganisms for aerobic digestion of sludge.

US 2008/0305540 discloses a membrane based bioreactor wherein anaerobic bacteria that have the ability to convert syngas to ethanol or other liquids have formed biofilms on the outer surface of hydrophobic membranes with the syngas fed to the bacterial biofilm through the inner surface of the membrane. Such a bioreactor system has been able to directly convert the primary components of synthesis gas, CO and $H_2/CO_2$, to ethanol and other liquid products such as n-butanol, acetic acid and butyric acid. In these systems the gas flows through a porous region of a hydrophobic membrane and then reaches a biofilm which is hydrophilic. One drawback of this arrangement is that if water reaches and deposits/condenses on the hydrophobic porous region it will severely decrease the gas transfer rate. Since the biofilm grows on the outside of the membrane, this type of membrane system also lacks a direct means to promote the formation of a biofilm with an adequate thickness and control its performance.

Asymmetric membranes are known for use in a variety of membrane separations processes such as ultra and nano filtration. Asymmetric membranes are typically hydrophilic and have a relatively tight semi permeable "skin" layer on one side supported on a porous "spongy" polymer layer. U.S. Pat. Nos. 4,442,206 and 4,440,853 show the use of the "spongy" polymer layer in an asymmetric membrane to immobilize microorganisms for certain biological processes that use soluble carbon sources. However, the adaptation and use of such membranes for the anaerobic bioconversion of syngas to liquids has not been shown in the past.

SUMMARY OF THE INVENTION

It has been found that an asymmetric membrane when used to contain anaerobic microorganisms for converting syngas (herein defined to include any gas containing CO and/or a mixture of $CO_2$ and $H_2$ as its principal components) will provide a stable method for enhancing the production of liquid products such as ethanol, propanol, butanol, hexanol, and other chemicals from a syngas stream. A porous side of the asymmetric membrane, referred to herein as a bio-layer, provides pores that promote and control the growth of microorganism colonies therein while also exposing a surface over which to directly feed the microorganisms with syngas. Simultaneously, another layer of the asymmetric membrane having less permeability than the bio-layer, herein referred to as a hydration layer, permeates liquid from the opposite side of the asymmetric membrane.

The invention thus uses an asymmetric membrane to provide a multi-layer membrane structure having a highly porous bio-layer for retaining the microorganisms within its pores and one or more hydration layers for controlling the supply of water to and from the bio-layer. In its operation, syngas contacts one side of the asymmetric membrane through the bio-layer while a nutrient and product containing liquid contacts the other through the hydration layer. Either the bio-layer or hydration layer may comprise multiple layers. The bio-layer, the hydration layer and/or additional layers may also serve to occlude pore openings, extract products, and supply moisture and nutrients and provide a bioreactor system within the method of this invention. The result is a highly efficient and economical transfer of the syngas at essentially 100% utilization, overcoming limitations for the other fermentation methods and fermentor configurations.

During syngas fermentation with the method of this invention, carbon monoxide or hydrogen/carbon dioxide from the syngas diffuses into the bio-layer in the porous membrane wall and is converted by the immobilized microorganisms into ethanol or other water-soluble products, which is then diffused into the aqueous stream flowing over the hydration layer and carried out of the bioreactor. The immobilized microorganisms remain hydrated through contact with the aqueous stream that passes through the hydration layer.

Therefore, one or more less porous hydration layers of the asymmetric membrane located opposite the gas contacting side establish an interface to provide moisture and trace nutrients that travel from the liquid toward the contained microorganisms while also extracting liquid products from the microorganisms. The extracted liquid flows across the hydration layer and into the liquid medium. Thus the desired products and the syngas from which they are produced flow through the layers of the membrane in the same direction, from the highly porous bio-layer to the less porous hydration layer. The liquid that contacts the less porous layer circulates over the membrane's liquid contacting surface and out of the bioreactor to facilities for the removal of the desired products.

The bio-pores of the bio-layer retain microorganisms for the production of the products from the syngas. The bio-layer keeps the microorganisms concentrated in bio-pores while still in direct contact with the syngas through a gas contacting side of the bio-layer thereby keeping syngas components readily available to enhance production of ethanol and other soluble products by the retained microorganisms. The microorganisms may reside in the bio-layer in isolation or as a biofilm. Some protrusion of the microorganisms outside of the bio-pores and past the gas contacting surface will not stop the operation of the bioreactor system within the method. Slight outgrowth of the microorganisms does not plug the gas flow path. Desirably however, the thickness of the bio-layer will dictate the thickness of any biofilm or colony of microorganisms so that the microorganisms fill up the bio-pores to the surface level of the bio-layer's gas contacting side. This permits pre-engineering of the microorganisms into a layer with a thickness that matches the thickness of the bio-layer wall. It also provides the added advantage of keeping microorganisms well confined and preventing their catastrophic loss.

Confinement works well with the microorganisms that are used for such anaerobic bioconversion of syngas components. These microorganisms grow slowly, produce product at the stationary phase and do not produce excess gas. Thus they are particularly suitable of use in the bio-pores because they will not destroy the membrane.

The bio-layer provides significant advantages in the utilization of syngas. Retaining the microorganisms in the bio-pores provides direct contact and gas transfer with the syngas. This eliminates any gas transfer resistance though a non-porous membrane layer or from wetting of the membrane pores.

Placing the hydration layer between the microorganisms and the liquid simplifies the operation of downstream separation facilities. The hydration layer provides a substantial barrier between the microorganisms and the product containing liquid that keeps the liquid flowing to separation facilities free of microorganisms and other biological contaminants. Eliminating biological contaminants from the liquid effluent removes the need for filtering and/or recycling of such materials.

The asymmetric membrane may be formed from any material or assemblage of materials that provide a bio-layer and a hydration layer with the functionality as described. In one form the bio-layer comprise hydrophilic materials that readily supply moisture throughout the bio-pores and up to the surface of the bio-layer's gas contacting side. The use of hydrophilic materials for the less porous hydration layer will enhance performance of the membrane by allowing easy movement of the water through the membrane. In many instances the bio-layer and the hydration layer will comprise the same material with the hydration layer taking the form of a skin on one side of the asymmetric membrane. Thus the biolayer and the hydration layer may have the same chemical composition. A hydration layer comprising a skin layer will normally also occludes the bio-pores to prevent migration of microorganisms into the liquid medium.

Utilization of the asymmetric membrane in this manner permits the bioreactor system to take on a variety of configurations. For example the asymmetric membrane may comprise hollow fibers or flat sheets whether in flat or spiral wound configurations. Suitable hollow fiber membranes may place the bio-layer or the hydration layer on the lumen side. Suitable housings may retain the membrane for co-current, counter-current, or cross-flow with respect to the circulation of the liquid on one side of the membrane and the bulk gas flow on the opposite side. In the case of hollow fibers, circulation of the syngas on the outside of the fibers facilitates a horizontal orientation of the fibers so that the bioreactor may work well whether extending in a principally horizontal or vertical direction.

This invention also improves operations for the circulation of liquid on the lumen side of hollow membranes by providing a well defined liquid flow path and providing a contiguous space for gas flow on the outside of the membrane. This permits very high density packing of the asymmetric membrane elements without fear of disrupting liquid flow patterns and creating stagnant areas for the circulating fluid. As a result the bioreactor system requires an overall smaller working volume than other proposed methods for conversion of syngas by fermentation.

Accordingly, in a broad form this invention is a bioreactor system for converting a feed gas containing at least one of CO or a mixture of $CO_2$ and $H_2$ to a liquid product under anaerobic conditions and delivering the liquid product to a product containing liquid. The system uses an asymmetric hydrophilic membrane having a gas contacting side in contact with the feed gas and a liquid contacting side in contact with the product containing liquid. The membrane has a bio-layer defining a plurality of bio-pores having effective diameters of at least 1 μm over at least a portion of the pore length for retaining microorganisms therein and a porous surface on the bio-layer. The porous surface of the bio-layer defines the gas contacting side and presents the openings of the bio-pores to the feed gas. The membrane also has a hydration layer that controls the flow of product containing liquid from the bio-layer and defines the liquid contact side of the membrane. Thus, the asymmetric membrane is arranged to transport the feed gas and the liquid products in co-directional flow from the gas contacting side to the liquid contacting side. In the system a feed gas supply conduit supplies feed gas and a feed gas chamber communicates with the gas supply conduit and the gas contacting side of the membrane for supplying feed gas to microorganisms retained in the bio-pores. A liquid circulation chamber communicates fluid with the liquid contacting side of the membrane for supplying water and nutrients to the microorganisms. A liquid recovering conduit transfers liquid products from the liquid circulation chamber.

In another form this invention includes the preferential removal of the carbon dioxide ($CO_2$) gas that is formed in the bioconversion method from the syngas. Such arrangement may use an enrichment membrane that selectively permeates $CO_2$ and then returns the syngas enriched in CO and $H_2$ to the bioreactor.

In yet another form of this invention the syngas may pass through multiple banks of asymmetric membranes in parallel or serial flow. A particularly useful form of the invention includes the preferential removal of the carbon dioxide ($CO_2$) gas that is formed in the bioconversion method from the syngas as it passes serially through multiple banks of asymmetric membranes.

A more specific form of the invention comprises a bioreactor system for converting a synthesis gas to a liquid product that includes a gas supply conduit for delivering synthesis gas, a gas distribution chamber in fluid communication with the gas supply conduit, and a liquid supply conduit for supplying fermentation liquid having a redox potential of less than −200 mV. A plurality of hollow fiber membranes disposed in the gas distribution chamber having inlet ends of the lumens in fluid communication with the liquid supply conduit and outer surfaces in fluid communication with the gas distribution chamber. The hollow fibers comprising asymmetric membranes having an outer polymer layer defining bio-pores with effective diameters in a range of from 1 μm to 100 μm for the retaining microorganisms therein. The microorganisms produce liquid products from the synthesis gas and have an inner skin for permeating fermentation liquid to the polymer layer and permeating liquid products from the polymer layer to the fermentation liquid. A liquid recovery conduit in fluid communication with the outlet ends of the hollow fiber lumens recovers fermentation liquid containing liquid products.

A yet more specific form of the invention comprises a bioreactor system for converting a synthesis gas to a liquid product. The system uses a gas supply conduit for delivering synthesis gas having an oxygen concentration of less than 100 ppm, a gas distribution chamber in fluid communication with the gas supply conduit, and a liquid supply conduit for supplying fermentation liquid having a redox potential of less than −200 mV. A plurality of hollow fiber membranes disposed in the gas distribution chamber have first lumen ends in fluid communication with the liquid supply conduit and second lumen ends for discharging liquid from the lumens. The outer surfaces of the hollow fibers are in fluid communication with the gas distribution chamber. The hollow fibers comprise asymmetric membranes with an inner skin made of a semi-permeable skin having a thickness of less 10 μm and a molecular weight cutoff (MWCO) range of from 10 to 300 kiloDalton (kDa) nominal MWCO. The skin is cast on the inside of a porous polymer having a thickness between 50 to 500 μm and bio-pores with effective diameters in a range of from 1 μm to 100 μm for the retaining microorganisms therein that produce ethanol from the synthesis gas. A liquid recovery conduit communicates fluid with the second lumen ends of the hollow fiber membranes to recover fermentation liquid containing liquid product.

A method form of the invention converts a feed gas containing at least one of CO or a mixture of $CO_2$ and $H_2$ to a liquid product comprising a $C_1$ to $C_6$ oxygenate under anaerobic conditions. The method passes the feed gas to a gas contacting side of an asymmetric hydrophilic membrane that defines a bio-layer comprising a plurality of bio-pores open to the gas contacting side and having effective diameters of at least 1 μm the asymmetric hydrophilic membrane also defines a hydration layer comprising a material that has a permeability less than permeability of the biolayer that controls the flow of liquid to and from the biolayer. The bio-pores retain an anaerobic microorganism for producing the liquid product by contact of the feed gas with the microorganisms. A fermentation liquid passes to a liquid contacting side of the hydration layer to permeate a portion of the fermentation liquid from the liquid contacting side into the bio-pores and into contact with the microorganisms. Contact of the liquid product with the fermentation liquid withdraws the liquid product from the microorganisms so that the liquid product flows with the fermentation liquid from the bio-pores to the liquid contacting surface and the feed gas and the liquid product are in co-directional flow. The method then recovers a fermentation liquid containing the liquid product from the from the liquid contacting side and separates the liquid product from the fermentation liquid to recover the liquid product.

A further method form of the invention converts a feed gas containing at least one of CO or a mixture of $CO_2$ and $H_2$ to a liquid product comprising ethanol under anaerobic conditions by passing the feed gas to a gas distribution chamber and distributing the feed gas the outer surface of a plurality of hollow fiber membranes disposed in the gas distribution chamber. Each fiber defines a bio-layer comprising a porous polymer having a thickness of at least 50 μm and a plurality of bio-pores having effective diameters of from 1 to 100 μm that open to the outer surface of the fibers. Each fiber also defines a hydration layer about the lumen of the fiber comprising a material that has a permeability less than permeability of the biolayer and that controls the flow of liquid to and from the biolayer. The bio-pores retain a mono-culture or a co-culture of microorganisms comprising at least one of *Clostridium ragsdalei, Butyribacterium methylotrophicum, Clostridium Ljungdahlii, Clostridium coskatii* and *Clostridium carboxidivorans* and producing ethanol by contact of the feed gas with the microorganisms. The method passes a fermentation liquid having a redox potential of less than −200 mV into the lumens of the fibers and into contact with a liquid contacting side of the hydration layer to permeate a portion of the fermentation liquid from the liquid contacting side into the bio-pores and into contact with the microorganisms. Contact of the microorganisms with the fermentation liquid withdraws the ethanol so that it flows with the fermentation liquid from the bio-pores to the liquid contacting surface and the feed gas and the ethanol are in co-directional flow. The method recovers a fermentation liquid containing the liquid product from the lumens of the fibers and separates the liquid product from the fermentation liquid to recover the liquid product.

DETAILED DESCRIPTION OF THE INVENTION

Bioconversions of CO and $H_2/CO_2$ to acetic acid, ethanol and other products are well known. For example, in a recent book concise description of biochemical pathways and energetics of such bioconversions have been summarized by Das, A. and L. G. Ljungdahl, Electron Transport System in Acetogens and by Drake, H. L. and K. Kusel, Diverse Physiologic Potential of Acetogens, appearing respectively as Chapters 14 and 13 of Biochemistry and Physiology of Anaerobic Bacteria, L. G. Ljungdahl eds,. Springer (2003). Any suitable microorganisms that have the ability to convert the syngas components: CO, H2, $CO_2$ individually or in combination with each other or with other components that are typically present in syngas may be utilized. Suitable microorganisms and/or growth conditions may include those disclosed in US 20070275447, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. Pat. No. 7,704,723 B2 which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol. U.S. Ser. No. 12/727,320 filed Mar. 20, 2010, entitled "A Novel Ethanologenic *Clostridium* Species, *Clostridium coskatii*" discloses a biologically pure culture of the microorganism *Clostridium Coskatii* having all of the identifying characteristics of ATCC No. PTA-10522 that may also be used to convert syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahli*, with strains having the identifying characteristics of ATCC 49587 (U.S. Pat. No. 5,173,429) and ATCC 55988 and 55989 (U.S. Pat. No. 6,136,577) and this will enable the production of ethanol as well as acetic acid. All of these references are incorporated herein in their entirety.

The microorganisms discovered to date can produce a variety of alcohols and oxoacids with a high degree of specificity. The method is generally suited for the production of $C_1$ to $C_6$ alcohols and oxoacids. Of these compounds ethanol, propanol, propionic acid, n-butanol, hexanol, acetic acid, and butyric acid are of most interest. The preferred product or production by this method is ethanol.

The microorganisms found suitable thus far for this invention require anaerobic growth conditions. Therefore the method will employ suitable control and sealing methods to limit the introduction of oxygen into the bioreactor. Since the microorganisms contact the liquid that circulates through the bioreactor, a suitable redox potential will be maintained and monitored to make insure anaerobic conditions. Anaerobic conditions in the liquid volume are usually defined as having a redox potential of less than −200 mV and preferably a redox potential in the range of from −300 to −500 mV. To further minimize exposure of the microorganisms to oxygen, the feed gas will preferably have an oxygen concentration of less than 1000 ppm, more preferably less than 100 ppm, and even more preferably less than 10 ppm.

The invention uses asymmetric membranes having a porous layer and a less permeable layer. The porous layer, referred to as the bio-layer may comprise any material suitable for the formation of the bio-pores and the transport of liquid to and away from the microorganisms in the bio-pores. The less porous layer, referred to as the hydration layer will control the transport of the fermentation liquid to and from the bio-layer for nourishing the microorganisms and maintain effluent products at desired concentrations. The bio-layer and hydration layer are described as single layers but either may comprise several layers.

The asymmetric membrane also requires material that will provide support to the membrane structure and will occlude the internal end of the bio-pores to prevent microorganisms and other biological material from passing into the fermentation liquid. The asymmetric membrane may contain additional layers for internal support and formation of the bio-pores or the bio-layer and/or hydration layer may serve these functions as well. Any additional layers must permit direct contact of syngas with the microorganisms in the bio-pores and the permeation of liquid into the bio-layer.

The bio-layer must define the bio-pores for retaining the microorganisms in direct contact with the syngas. The biopores require an effective diameter of at least 1 µm over at least a portion of its length. The term effective diameter refers to the open cross-sectional area of a regularly shaped pore that would provide the same cross sectional area. The pores need not have a uniform cross section and bio-pores having an effective diameter of 1 µm over at least a third of its length will work well. The size of the bio-pores in the bio-layer of the membrane will usually have an effective diameter substantially greater than 1 µm, preferably in the range of 2 to 100 µm, and most preferably in the range of 5 to 50 µm. Typical depths of the bio-pores range from 50 to 500 µm which generally corresponds to the thickness of the bio-layer.

At minimum the hydration layer must have restricted liquid permeability with respect to the biolayer. The restricted permeability prevents excessive fermentation liquid from migrating into the bio-layer during normal operation of the method and interfering with contact between the gas and microorganisms. In most cases the hydration layer will comprise a higher density material than the bio-layer that restricts liquid flow while also occluding the internal end of the bio-pores to block migration of the microorganisms into the fermentation liquid.

Particularly suitable forms of asymmetric membranes are porous membranes with a tight (i.e., having small pores) thin "skin" on one surface of the membrane that provides the hydration layer and a relatively open support structure underneath the skin that provides the bio-layer and defines the bio-pores. The skin will typically comprise a semi-permeable layer having a thickness of from 0.5 to 10 µm. The skinned asymmetric membrane can include an "integrally skinned" membrane prepared by using phase inversion of one polymer or a composite membrane, where a thin layer of a certain material is formed on top of a porous sublayer of a same or different material. General description of asymmetric membranes and methods of their preparation can be found in the literature (e.g., Cheryn, M., Ultrafiltration and Microfiltration Handbook, Technomics Publishing Company, Lancaster, Pa., 1998; and Mulder, M., Basic Principles of Membrane Technology, 2.sup.nd Edition, Kluwer Academic Publishers, Norwell, Mass., 1996).

A suitable skin layer has a pore size that is smaller than the size of microbial cells to prevent the cells from passing through the membrane skin but the opposite surface of the membrane has large openings that allow cells to enter and leave the bio-pores of the membrane wall. Typically, the pore size of the skin layer is less than 0.5 µm, preferably less than 0.25 µm, and most preferably in the ultrafiltration range of nominal MWCO of 10 to 300 kDa and more preferably in the range of 10 to 100 kDa.

Several asymmetric ultrafiltration membranes are available from Millipore Corporation (Bedford, Mass.), including but not limited to the Amicon Membranes and the Ultracel PLC Membranes. The Amicon Membranes are made of polyethersulfone and with a range of a nominal MWCO of 30 kDa for Amicon PM30. The Ultracel PLC Membranes, which are composite membranes made from casting the regenerated cellulose membrane onto a microporous polyethylene substrate, are available in the pore size range from 5 kDa (PLCCC) to 1000 kDa (PLCXK). Additional examples of asymmetric membranes are the MMM-Asymmetric Super-Micron Membranes and BTS Highly Asymmetric Membranes, both available from Pall Corporation (East Hills, N.Y.). The MMM-Asymmetric Membranes, available in pore size range from 0.1 to 20.0 µm, are made of polysulfone and polyvinylpyrrolidone. The BTS Highly Asymmetric Membranes, available in pore size range from 0.05 to 0.80 µm, are cast of polysulfone with a "cut off" layer of about 10 µm and a total thickness of about 120 µm.

Hollow fiber membrane modules containing asymmetric ultrafiltration membranes are commercially available from a number of membrane manufacturers. For example, the Kros-Flo® Max Module Model KM5S-800-ON from Spectrum Laboratories (Rancho Dominguez, Calif.) has 22.0 $m^2$ membrane surface area of asymmetric polysulfone hollow fiber membranes with 0.5 mm fiber inner diameter, a tight skin on the lumen side, and a pore rating of 50 kDa. ROMICON® polysulfone hollow fiber membranes available from Koch Membrane Systems (Wilmington, Mass.) are also asymmetric with the tight skin on the lumen side. ROMICON cartridge Model HF-97-43-PM50 is a 6-inch module containing fibers of 1.1 mm inner diameter and 50 kDa nominal MWC at 9.0 $m^2$ total membrane surface area.

Membranes of the various geometries and compositions described above may be used in arrangements of unitary arrays or assemblies of varied composition in the method of this invention. Any suitable potting technique can be used to collect and provide the necessary assembly of individual membrane elements. In such membranes the gas and liquid can be brought into direct and intimate contact at the gas contact surface of the bio-layer. Liquid is passed in the liquid side of the membranes via pumping, stifling or similar means to remove the ethanol and other soluble products formed; the products are recovered via a variety of suitable methods.

The syngas flows through the gas chamber or channels of the bioreactor system continuously or intermittently. The feed gas pressure is in the range of 1 to 1000 psig, preferably 5 to 400 psig, and most preferably 10 to 200 psig. Operating at higher gas pressures has the advantage of increasing the solubilities of gases in the liquid and potentially increasing the rates of gas transfer and bioconversion. The differential pressure between the liquid and gas phases is managed in a manner that the membrane integrity is not compromised (e.g., the burst strength of the membrane is not exceeded) and the desired gas-liquid interface phase is maintained.

The gas side pressure is normally slightly higher than the liquid pressure to prevent convective liquid flow from the hydration layer (liquid) side to the open surface (gas) of the gas contacting side. The higher pressure also avoids formation of a liquid layer at the cell/gas interface, which would impede gas transfer to the cells.

When the feed syngas contains moisture, condensation of water can occur at the microorganism/gas interface as consumption of syngas results in supersaturation of water. This condensed water leaves the cell/gas interface by dripping to the bottom of the bioreactor due to gravity as well as by convective flow through the membrane due to the slightly higher pressure of the gas.

Figure 1:
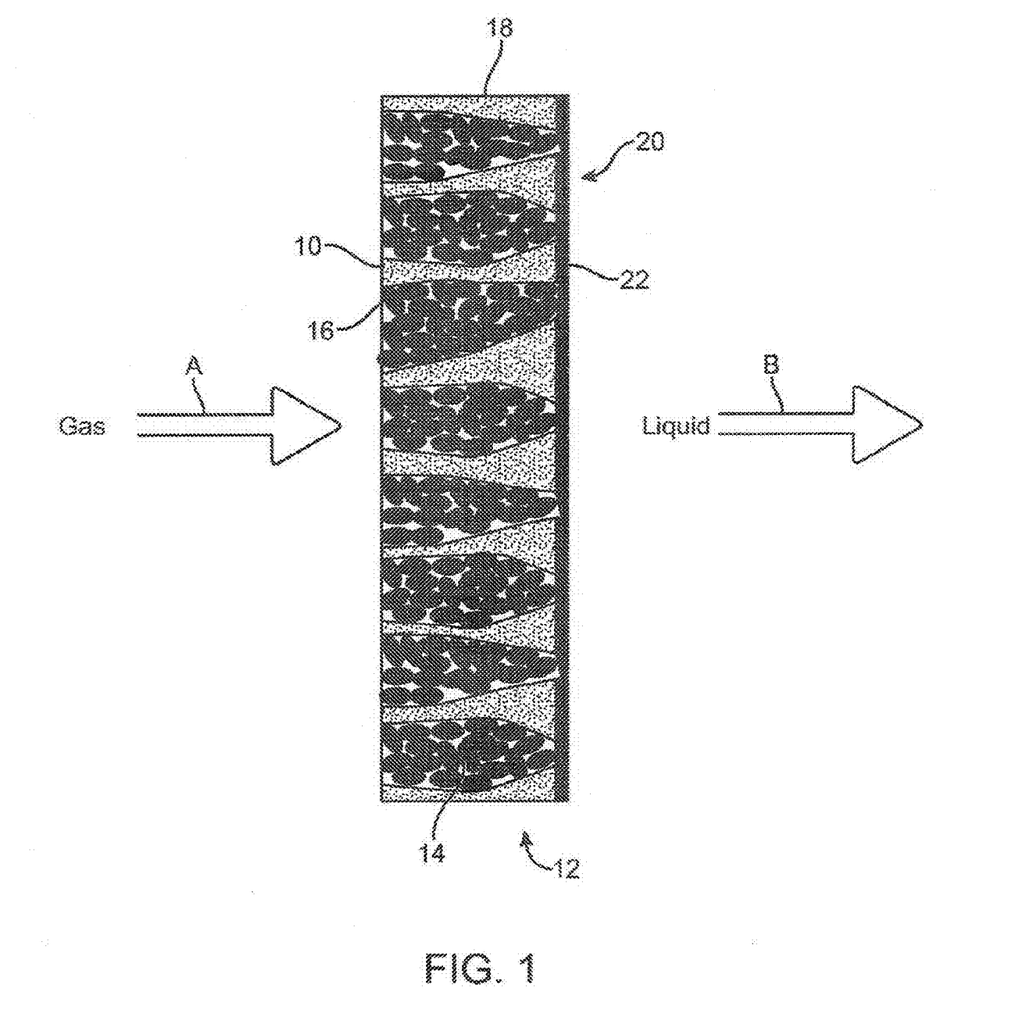
FIG. 1 is a schematic drawing showing a cross section of an asymmetric membrane with gas stream in contact with a bio-layer that retains microorganisms therein and a hydration layer in the form of a skin in contact with liquid.

In this invention, an asymmetric membrane, suitable for permeation of the fermentation liquid provides the separation between the liquid phase and feed gas comprising at least one of CO or a mixture of $H_2$ and $CO_2$ and a liquid phase. FIG. 1 shows more detail of the membrane configuration and interface in the operation of a representative bio-reactor system that uses the method of this invention. FIG. 1 depicts a cross section of a single membrane element with a syngas stream A flowing to the gas contacting side 10 of the asymmetric membrane 12. The syngas components directly contact the microorganisms 14 contained in bio-pores 16. The anaerobic acetogenic bacteria, *Clostridium ragsdaeli*, having all of the identifying characteristics of ATCC No. BAA-622, is maintained in the biopores and supplied with the fermentation liquid by permeation through the bio-layer 18. The fermentation liquid circulates on the opposite side of the syngas A and permeates through a hydration layer formed as skin 20 on the inner surface of bio-layer 18. Direct contact of skin 20 with bio-layer 18 transfers the fermentation liquid to the bio-pores 16. The surfaces of bio-layer 18 that contact the microorganisms and gas stream serve as equilibrium partitioning across the asymmetric membrane to keep the liquid and gas phases separated from each other. The pores in skin 20 are much smaller than the width of the microorganisms retained in bio-pores 16 so that skin 20 occludes the inner end of bio-pores 16 and prevents the microorganisms from passing through skin 20 and to liquid contacting surface 22. As a result the microorganisms 14 preferentially stay within bio-pores 16 to gain metabolic energy by converting CO and $H_2/CO_2$ thereby growing and sustaining themselves within the bio-pores 16. A portion of liquid B is withdrawn and separated to recover the desired products from the fermentation liquid.

To load the asymmetric membrane with microorganisms, the bio-layer first is inoculated with microorganisms followed by further cell growth to reach the desired cell loading density. To inoculate the bio-layer, an aqueous solution containing microorganisms is introduced to the gas contacting side of the asymmetric membrane, and then the solution is slowly filtered through the bio-layer and hydration layer by applying a slight trans-membrane pressure, creating a microorganism-free filtrate through the hydration layer and entrapping cells within the bio-pores of the bio-layer. The microorganism-containing membrane is incubated for further microorganism growth, by contacting the membrane with a liquid solution containing nutrients and a carbon source suitable for microorganism growth. Alternatively, the membrane can be incubated using a syngas and a liquid solution containing nutrients.

Figure 2A:
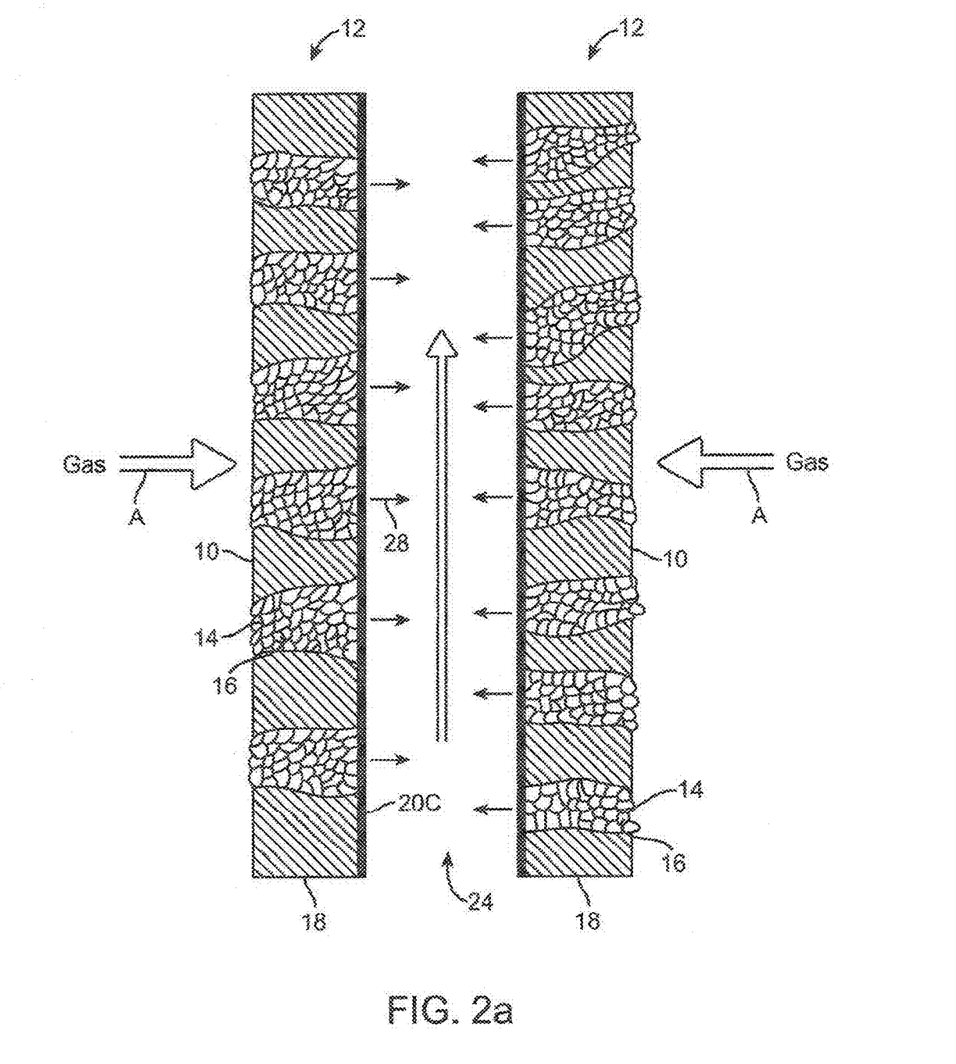
FIG. 2a is a schematic drawing showing a central passage formed by two membranes of the type shown in FIG. 1 with a gas stream contacting the outer wall and liquid contacting the inner walls.
Figure 2B:
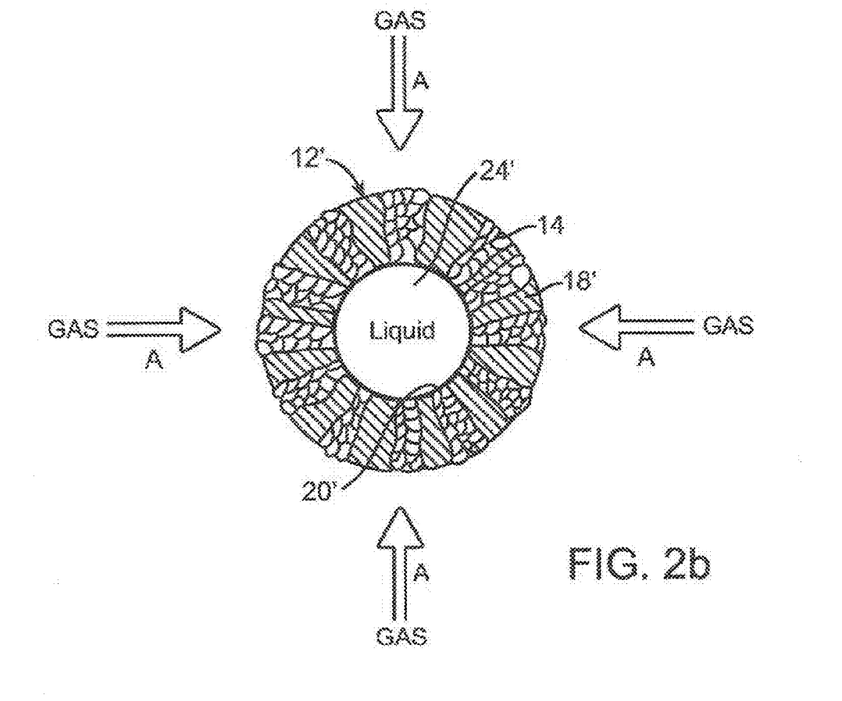
FIG. 2b is a schematic drawing showing a transverse cross-section of the asymmetric membrane of FIG. 1 made into a hollow fiber with the bio-layer on the outside and the hydration layer on the inside.
Figure 2C:
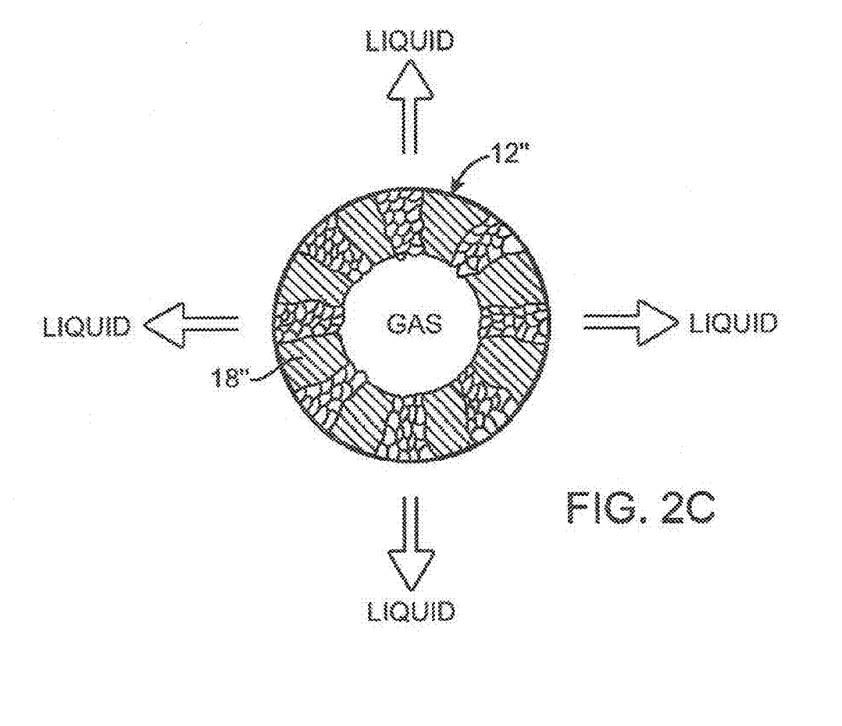
FIG. 2c shows a hollow fiber membrane modified to have the hydration layer on the outside and the bio-layer on the inside.

FIGS. 2a-c show various configurations of asymmetric membranes with microorganisms present within bio-pores of the bio-layers. In FIG. 2a two asymmetric membrane portions 12 border a central liquid channel 24 through which a fermentation liquid circulates in the direction of stream C. The asymmetric membranes on each side of liquid channel 24 functions in a similar manner to that described for the single membrane element of FIG. 1. Syngas flows across gas contacting side 10 into contact with microorganisms 14 and fermentation products passing out skin 20 in the direction of arrows 26. The arrangement of FIG. 2a can use a flat sheet configuration or a tubular configuration and be particularly useful for good flow control and distribution on the liquid side.

FIG. 2b shows a special case of FIG. 2a wherein the asymmetric membrane 12' wraps around in continuous form to provide a tubular membrane with a central liquid channel 24'. In this case the syngas stream A flows radially inward into contact with the microorganisms 14 contained within an annular bio-layer 18'. The skin 20' covers the inner surface of biolayer 18' and controls the permeation of liquid across biolayer 18'.

FIG. 2c again shows a tubular configuration for an asymmetric membrane but this time with the skin and bio-layer locations reversed from that of FIG. 2b. In the case of FIG. 2c, liquid contacts the outer surface of the asymmetric membrane 12" and liquid permeates to the bio-layer located inside membrane 12". The central passage 24" now serves to supply the syngas to the inner surface of the membrane.

In most operations the membrane arrangements will benefit from occasional purging or flushing of the bio-pores and gas contacting surfaces. For this purpose, periodically during syngas fermentation, the liquid pressure can be increased for a short time to become slightly higher than the gas pressure to create a liquid flow, comprising mainly fermentation water, through the membrane to purge some accumulated dead microorganisms or biopolymers out from the bio-pores and from the gas contacting surface. This liquid, primarily water, is collected from the gas stream side of the bioreactor. Optionally this liquid stream may be treated for removal of suspended solids and recirculated to the bioreactor.

Usually it is also desirable to clean the bio-pores and bio-layer. This method begins with substantially removing the immobilized cells and the cleaning the membrane. To do this the gas supply is stopped, and the membrane is cleaned with cleaning solutions in manners similar to typical cleaning of microfiltration and ultrafiltration membranes. For example, the asymmetric membrane is first soaked in a cleaning solution from both the sides, e.g. the bio-layer and hydration layer. The cleaning solution is formulated or selected to facilitate solubilization of microorganism and biopolymers. One of such solutions is an aqueous solution containing 2% NaCl and 0.4% NaOH, but many other formulations have been used for membrane cleaning, including some containing surfactants and hydrolytic enzymes. After soaking, the cleaning solution is circulated and a positive trans-membrane pressure is applied from the hydration layer side to create a convective flow through the membrane and flush microorganism and biopolymers out through the gas contacting surface of the bio-layer. The soaking-filtration procedures can be repeated as needed, and different cleaning solutions can be used. After membrane cleaning, the membrane can be used for loading and growing new cells for syngas fermentation again.

Figure 3:
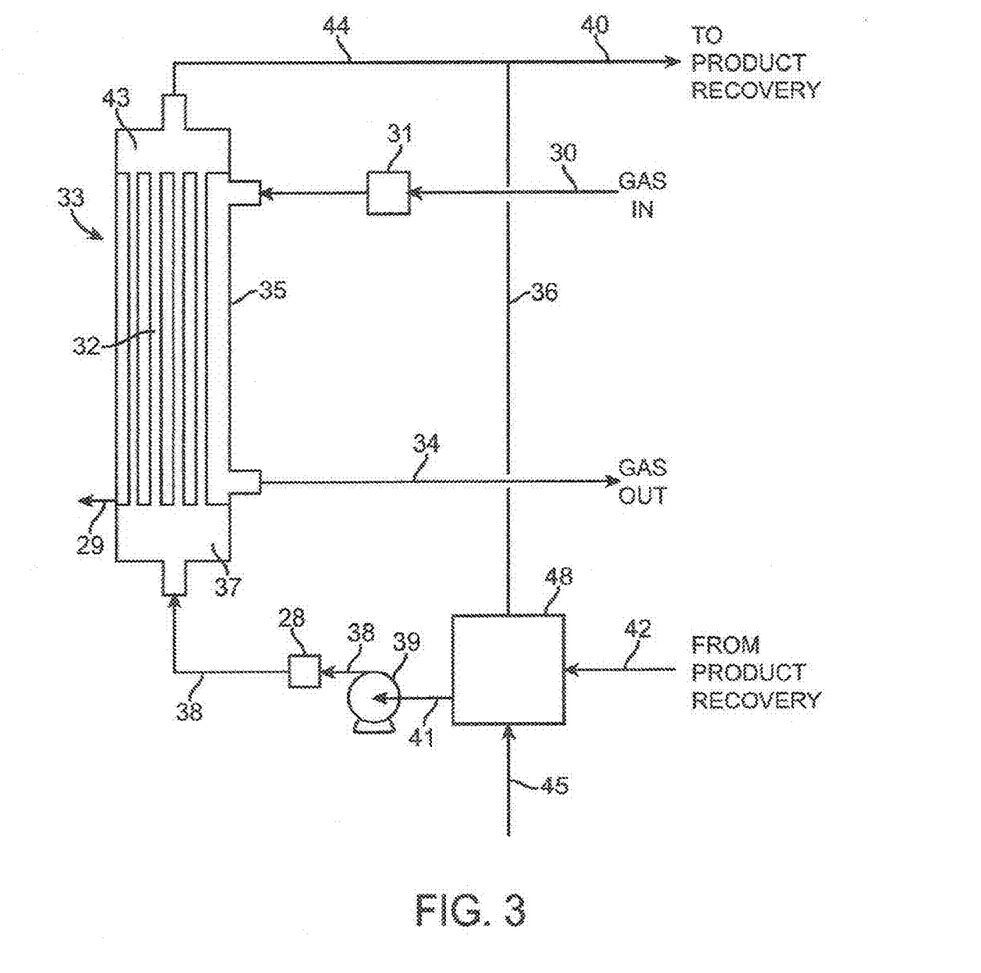
FIG. 3 is a schematic drawing of a bioreactor system showing gas and liquid circulation.

FIG. 3 illustrates a specific configuration of a bio-reactor method utilizing a membrane containing microorganisms. A gas supply conduit delivers a feed gas stream 30 containing syngas at a rate recorded by a flow meter 31 to a bioreactor 33. The bioreactor 33 includes a vessel 35 that surrounds the outside of the tubular membrane elements 32. Membrane elements 32 contain bio-pores to promote growth and maintenance of microorganisms within a bio-layer of the membrane elements.

A feed gas distribution chamber 35 receives the feed gas stream and distributes it into direct contact with the outer surface of the membrane elements 32. The feed gas exits the vessel 35 via a line 34 such that a continuous addition of feed gas is established around the outer surface of membrane elements 32. The relative locations of the feed gas lines provide a downward direction of the bulk gas flow in the bioreactor 33.

Vessel 35 also contains a line 29 for draining liquid. Liquid may accumulate at the bottom of the vessel 35 for a variety of reasons as previously described such as condensation from moisture in the gas, flushing or purging of the membrane elements or periodic cleaning operations. Alternately line 29 may provide an outlet for liquid drainage. Liquid from condensation or flushing may be withdrawn from either location and treated for return to the fermentation liquid.

Fermentation liquid enters bioreactor 33 via a conduit 38 under pressure supplied by a pump 39 and at rate recorded by a flow meter 28. A chamber 37 distributes fermentation liquid to the tubular membranes 32 via the bottom ends of the lumens. At the top end of bioreactor 33 a chamber 43 collects the fermentation liquid from the top of the lumens for withdrawal of the liquid via a conduit 44. The relative locations of chambers 37 and 43 establish upward flow of the liquid through bioreactor 33 so that there is countercurrent flow with respect to the bulk gas flow and the liquid flow.

A line 40 withdraws a net portion of the liquid from line 44 while the remainder of the liquid returns to the bioreactor 33 via a recirculation line 36 and mixing chamber 48, a line 41 and line 38. Line 40 carries the liquid to product recovery facilities that recover liquid products. Depending on the nature of the desired product, there are a number of technologies that can be used for product recovery. For example, distillation, dephlegmation, pervaporation and liquid-liquid extraction can be used for the recovery of ethanol and n-butanol, whereas electrodialysis and ion-exchange can be used for the recovery of acetate, butyrate, and other ionic products. In all cases the product recovery step removes the desirable product from stream 40, while leaving substantial amounts of water and residual nutrients in the treated stream, part of which is returned to the bioreactor system via line 42 and mixing chamber 48.

Means for temperature and pH control for the liquid can be added anywhere along the re-circulating liquid loop, which consists of lines 38, 44, 36, and 41 as well as chambers 37, 43, and 48. A line 45 provides the nutrients needed to sustain the activity of the microorganisms to the re-circulating liquid loop chamber 48. Chamber 48 provides mixing of the nutrients and the other streams.

The flow rates of Streams 38 and 44, recirculated through the membrane unit, are selected so that there is no significant liquid boundary layer that impedes mass transfer near the liquid-facing side of the membrane. The superficial linear velocity of the liquid tangential to the membrane should be in the range of 0.01 to 20 cm/s, preferably 0.05 to 5 cm/s, and most preferably 0.2 to 1.0 cm/s.

In all the depicted arrangements the CO and $H_2/CO_2$ from the syngas are utilized and a gradient for their transport from the gas feed side is created due to biochemical reaction on the membrane liquid interface. This reaction creates liquid fuel or chemicals such as ethanol and acetic acid which diffuse into the liquid and are removed via circulation of the liquid with the hydration layer of the asymmetric membrane. Thus the very large surface areas of the membrane pores are usable for gas transfer to the microorganisms and the product is recovered from the liquid side. Furthermore, the reaction rate, gas concentration gradient and the thickness of the microorganisms can be maintained in equilibrium because the microorganisms will maintain themselves only up to the layer where the gas is available as a result of the inherently slow growth characteristics of the microorganisms that metabolize syngas components.

The membranes can be configured into typical modules as shown as an example in FIG. 3 for hollow fibers. The gas flows in the fine fibers that are bundled and potted inside a cylindrical shell or vessel through which the liquid is distributed and circulated. Very high surface areas in the range of 1000 $m_2$ to 5000 $m^2$ per $m^3$ can be achieved in such modules.

During the bioconversion excess $CO_2$ is generated and this gas can diffuse back and dilute out the concentrations of CO and $H_2$ in the feed gas and thus reduce their mass transfer rates. Other types of membranes that preferentially permeate $CO_2$ over CO and $H_2$ can be used in the multi stage configuration as shown as an example in FIG. 4 where, using a membrane that selectively permeates $CO_2$ and then returning the syngas enriched in CO and $H_2$ to the bioreactor can be achieved.

Figure 4:
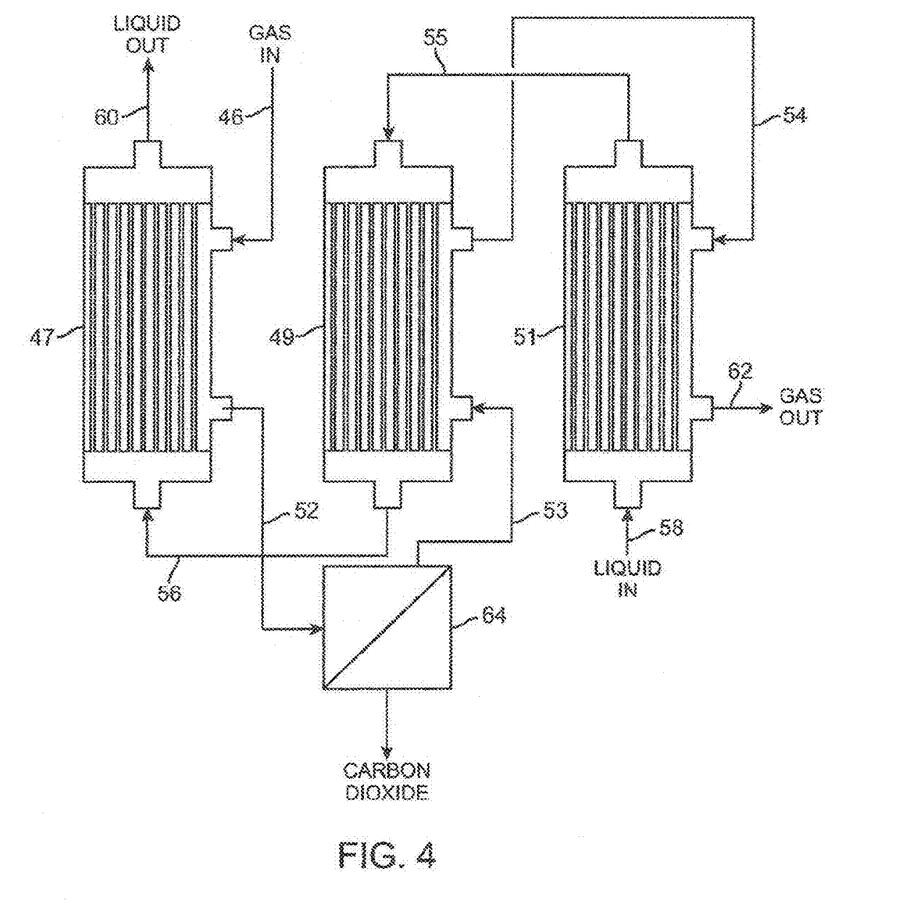
FIG. 4 is a schematic drawing showing a bioreactor system with multiple bioreactors arranged in series having intermediate carbon dioxide removal.

FIG. 4 depicts a method where the entering feed gas flows into bioreactor 47 via line 46 and serially through bioreactors 49 and 51 via lines 52, 53 and 54. At the same time liquid that contacts the microorganisms enters bioreactor 51 via line 58 and flows countercurrently, with respect to the gas flow, through bioreactors 47, 49 and 51 via lines 55 and 56. Liquid products are recovered from the liquid flowing out of line 60 and a gas stream is withdrawn from bioreactor 51 via line 62. Separation unit 64 provides the stream of line 56 with intermediate removal of $CO_2$ from the process via any suitable device or method such as a membrane or extraction step. Interconnecting lines 55 and 56 also provide the function of establishing continuous communication through all of the lumens of the different bioreactors so that any combined collection and distribution chambers provide a continuous flow path.

Example 1

A Romicon® membrane cartridge Model CTG, 1" HF 1.0-43-PM-10 from Koch Membrane Systems (Wilmington, Mass.) is used as a membrane bioreactor for the conversion of carbon monoxide and hydrogen into ethanol. This membrane cartridge contains asymmetric polysulfone hollow fibers with 1.1 mm inner diameter and rated at 10 kDa nominal MWCO. The active membrane surface area of the module is 0.093 m.sup.2. The thickness of the bio-pore layer is approximately 400 μm with an effective bio-pore diameters in the range of 10 to 100 μm. The temperature of the membrane cartridge is maintained at 37° C. with flexible heater attached around the cartridge and regulated with a temperature controller. The membrane cartridge has a fiber holdup volume (total volume of the fibers including the lumens) of 90 $cm^3$. The fibers occupy a chamber in the cartridge having a total volume of 180 $cm^3$.

The membrane module is connected to a 7.5-liter BioFlo® 310 Fermentor from New Brunswick Scientific (Edison, N.J.). The fermentor contains 3 liters of the fermentation medium, which is agitated at 100 rpm and maintained at 37° C. and pH 5.9 with 1 N NaOH and 1 N HCl. The fermentation medium has the compositions shown in Tables 1&2. The medium is pumped from the fermentor, flows through the lumen side of the membrane module, and returns to the fermentor at a recirculation flow rate of 500 ml/min, unless otherwise stated. The fermentor is sparged with $N_2$ at 100 std ml/min initially to maintain anaerobic conditions and switched to syngas overlay as described below.

Initially, the membrane cartridge is inoculated with 150 ml of an active culture of *Clostridium ragsdalei* ATCC No. BAA-622 by injecting the inoculum into the shell space. The inoculum is slightly pressurized to allow excess liquid volume to pass through the membrane into the lumen and the microbial cells to enter the void space of the membrane wall. Subsequently, a gas containing 40% CO, 30% $H_2$, and 30% $CO_2$ is fed to the shell side of the membrane cartridge at about 5 psig to displace the remaining inoculum liquid. The gas continues to be fed at 300 std ml/min throughout the remainder of the fermentation run and the residual gas from the module is directed to the fermentor headspace and exits the fermentor through a condenser and a vent filter. The gas pressure in the shell side of the membrane cartridge is maintained at about 5 psi greater than the liquid pressure in the lumen by adjusting a back-pressure valve downstream the gas outlet of the membrane cartridge.

The module is first operated in the batch mode for 5 days to accumulate microbial cells within the porous membrane wall. Then, the module is switched to continuous operation, with continuous withdrawal of the fermentation liquid for product recovery and replenishing of fresh medium at 25 ml/hr. During the continuous operation, a "maintenance cycle" is performed for 30 minutes every one to three days. In the "maintenance cycle", the gas feed is stopped and the liquid circulation rate is increased to 2000 ml/min, resulting in a lumen liquid pressure 1-2 psi greater than shell side pressure and slow permeation of liquid into the shell space and draining out of the cartridge. At the end of the cycle, the liquid circulation rate is reduced back to 500 ml/min and the gas feed resumes. Excess biomass that may consist of dead cells and other biological material is purged out of the membrane cartridge with this "maintenance cycle." After 20 days of continuous operation, the ethanol concentration increases to 15 g/L.

TABLE 1

Fermentation Medium Compositions

| Components | Amount per liter |
| --- | --- |
| Mineral solution, See Table 2(a) | 25 ml |
| Trace metal solution, See Table 2(b) | 10 ml |
| Vitamins solution, See Table 2(c) | 10 ml |
| Yeast Extract | 0.5 g |
| Adjust pH with NaOH | 6.1 |
| Reducing agent, See Table 2(d) | 2.5 ml |

TABLE 2(a)

Mineral Solution

| Components | Concentration (g/L) |
| --- | --- |
| NaCl | 80 |
| NH$_4$Cl | 100 |
| KCl | 10 |
| KH$_2$PO$_4$ | 10 |
| MgSO$_4$•7H$_2$O | 20 |
| CaCl$_2$•2H$_2$O | 4 |

TABLE 2(b)

Trace Metals Solution

| Components | Concentration (g/L) |
| --- | --- |
| Nitrilotriacetic acid | 2.0 |
| Adjust the pH to 6.0 with KOH | |
| MnSO$_4$•H$_2$O | 1.0 |
| Fe(NH$_4$)$_2$(SO$_4$)$_2$•6H$_2$O | 0.8 |
| CoCl$_2$•6H$_2$O | 0.2 |
| ZnSO$_4$•7H$_2$O | 1.0 |
| NiCl$_2$•6H$_2$O | 0.2 |
| Na$_2$MoO$_4$•2H$_2$O | 0.02 |
| Na$_2$SeO$_4$ | 0.1 |
| Na$_2$WO$_4$ | 0.2 |

TABLE 2(c)

Vitamin Solution

| Components | Concentration (mg/L) |
| --- | --- |
| Pyridoxine•HCl | 10 |
| Thiamine•HCl | 5 |
| Roboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 5 |
| Biotin | 2 |
| Folic acid | 2 |

TABLE 2(d)

Reducing Agent

| Components | Concentration (g/L) |
| --- | --- |
| Cysteine (free base) | 40 |
| Na$_2$S•9H$_2$O | 40 |

Example 2

A MiniKros® membrane module Model M2-100S-601-01N from Spectrum Laboratories (Rancho Dominguez, Calif.) is used as a membrane bioreactor for the conversion of carbon monoxide and hydrogen into ethanol, acetate, butanol and butyrate. This membrane module contains asymmetric polysulfone hollow fibers with 1.0 mm inner diameter and a permeability rated at 100 kDa nominal MWCO. The active membrane surface area of the module is 0.32 m$^2$. The biolayer thickness is approximately 150 μm and the bio-pores have effective diameters in the range of 3 to 30 μm. The membrane cartridge has a fiber holdup volume of 200 cm$^3$. The fibers occupy a chamber in the cartridge having a total volume of 340 cm$^3$. The temperature of the membrane cartridge is maintained at 37° C. with flexible heater attached around the cartridge and regulated with a temperature controller.

The membrane module is connected to a 7.5-liter BioFlo® 310 Fermentor from New Brunswick Scientific (Edison, N.J.). The fermentor contains 3 liters of the fermentation medium, which is agitated at 100 rpm and maintained at 37° C. and pH 5.8 with 1 N NaOH and 1 N HCl. The fermentation medium has the compositions shown in Tables 3&4. The medium is pumped from the fermentor, flows through the lumen side of the membrane module, and returns to the fermentor at a recirculation flow rate of 1000 ml/min, unless otherwise stated. The fermentor is sparged with N$_2$ at 100 std ml/min initially to maintain anaerobic conditions and switched to syngas overlay as described below.

Initially, the membrane module is inoculated with 300 ml of an active culture of *Clostridium carboxidivorans* ATCC No. BAA-624 by injecting the inoculum into the shell space. The inoculum is slightly pressurized to allow excess liquid volume to pass through the membrane into the lumen and the microbial cells to enter the void space of the membrane wall. Subsequently, a gas containing 40% CO, 30% H$_2$, and 30% CO$_2$ is fed to the shell side of the membrane module at about 5 psig to displace the remaining inoculum liquid. The gas continues to be fed at 300 std ml/min throughout the remainder of the fermentation run and the residual gas from the module is directed to the fermentor headspace and exits the fermentor through a condenser and a vent filter. The gas pressure in the shell side of the membrane module is maintained at about 5 psi greater than the liquid pressure in the lumen by adjusting a back-pressure valve downstream the gas outlet of the membrane module.

The module is first operated in the batch mode for 5 days to accumulate microbial cells within the porous membrane wall. Then, the module is switched to continuous operation, with continuous withdrawal of the fermentation liquid for product recovery and replenish of fresh medium at 90 ml/hr. During the continuous operation, a "maintenance cycle" is performed for 30 minutes every one to three days. In the "maintenance cycle", the gas feed is stopped and the liquid circulation rate is increased to 3000 ml/min, resulting in a lumen liquid pressure 1-2 psi greater than shell side pressure and slow permeation of liquid into the shell space and draining out of the cartridge. At the end of the cycle, the liquid circulation rate is reduced back to 1000 ml/min and the gas feed resumes. Excess biomass that may consist of dead cells and other solids are purged out of the membrane cartridge with this "maintenance cycle." After 20 days of continuous operation, the withdrawn fermentation liquid contains 6.4 g/L ethanol, 2.5 g/L acetate, 4.8 g/L butanol and 1.5 g/L butyrate.

TABLE 3

Fermentation Medium Compositions

| Components | Amount per liter |
|---|---|
| Mineral solution, See Table 4(a) | 30 ml |
| Trace metal solution, See Table 4(b) | 10 ml |
| Vitamins solution, See Table 4(c) | 10 ml |
| Yeast Extract | 0.5 g |
| Adjust pH with NaOH | 6.1 |
| Reducing agent, See Table 4(d) | 5.0 ml |

TABLE 4(a)

Mineral Solution

| Components | Concentration (g/L) |
|---|---|
| NaCl | 40 |
| $NH_4Cl$ | 50 |
| KCl | 5 |
| $KH_2PO_4$ | 5 |
| $MgSO_4 \cdot 7H_2O$ | 10 |
| $CaCl_2 \cdot 2H_2O$ | 2 |

TABLE 4(b)

Trace Metals Solution

| Components | Concentration (g/L) |
|---|---|
| Nitrilotriacetic acid | 2.0 |
| Adjust the pH to 6.0 with KOH | |
| $MnSO_4 \cdot H_2O$ | 1.0 |
| $Fe(NH_4)_2(SO_4)_2 \cdot 6H_2O$ | 0.8 |
| $CoCl_2 \cdot 6H_2O$ | 0.2 |
| $ZnSO_4 \cdot 7H_2O$ | 0.2 |
| $NiCl_2 \cdot 6H_2O$ | 0.02 |
| $Na_2MoO_4 \cdot 2H_2O$ | 0.02 |
| $Na_2SeO_4$ | 0.02 |
| $Na_2WO_4$ | 0.02 |

TABLE 4(c)

Vitamin Solution

| Components | Concentration (mg/L) |
|---|---|
| Pyridoxine•HCl | 10 |
| Thiamine•HCl | 5 |
| Roboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 2 |
| Biotin | 2 |
| Folic acid | 2 |

The invention claimed is:

1. A method for converting a feed gas containing at least one of CO or a mixture of $CO_2$ and $H_2$ to a liquid product under anaerobic conditions, said method comprising:

a) passing the feed gas to a gas contacting side of an asymmetric hydrophilic membrane that defines a biolayer comprising an open surface presenting a plurality of bio-pores open to the gas contacting side and having effective diameters of at least 1 µm and that defines a hydration layer comprising a material that has a permeability less than permeability of the biolayer that controls the flow of liquid to and from the biolayer;

b) retaining an anaerobic microorganism in the bio-pores and producing the liquid product by contact of the feed gas with the microorganisms;

c) passing a fermentation liquid to a liquid contacting side of the hydration layer to permeate a portion of the fermentation liquid from the liquid contacting side into the bio-pores and into contact with the microorganisms;

d) withdrawing the liquid product from the microorganisms by contact of the liquid product with the fermentation liquid so that the liquid product flows with the fermentation liquid from the bio-pores to the liquid contacting surface and the feed gas and the liquid product are in co-directional flow;

e) maintaining the feed gas on the gas contacting side of the membrane at a pressure above the pressure of the fermentation liquid on the liquid contacting side of the membrane by an amount that prevents the convective liquid flow from the hydration layer to the open surface of the gas contacting side of the asymmetric membrane;

f) recovering a fermentation liquid containing the liquid product from the liquid contacting side; and, g) separating the liquid product from the fermentation liquid to recover the liquid product.

2. The method of claim 1 wherein the asymmetric membrane comprises a hydration layer in the form of a semi-permeable skin on a porous polymer that provides the biolayer, the semi-permeable skin having a thickness of less than 10 µm and defining the gas contact side of the member and the porous polymer layer having a thickness of at least 50 µm and defining the gas contact side of the membrane.

3. The method of claim 2 wherein the semi-permeable skin is rated at a nominal MWCO of less than 300 kDa and the porous polymer defines bio-pores with effective diameters that do not exceed 100 µm.

4. The method of claim 1 wherein the microorganism produces a liquid product comprising at least one of ethanol, propanol, n-butanol, hexanol, acetic acid, and butyric acid.

5. The method of claim 1 wherein the feed gas is synthesis gas having an oxygen concentration of less than 1000 ppm, the fermentation liquid has a redox potential of less than −200 mV, the bio-pores of the membrane retain a microorganism that produces ethanol and the liquid product comprises ethanol.

6. The method of claim 1 wherein the asymmetric membrane comprises a plurality of hollow fiber membranes.

7. The method of claim 6 wherein feed gas passes serially into contact with multiple asymmetric membranes and $CO_2$ is removed from the feed gas as it passes between the asymmetric hollow fiber membranes.

8. The method of claim 6 wherein the liquid product passes into and through the lumens of the asymmetric membrane and the feed gas passes across the asymmetric membrane countercurrent to the axial direction of the lumens.

9. The method of claim 1 wherein the microorganisms in the bio-pores comprise a mono-culture or a co-culture of at least one of *Clostridium ragsdalei, Butyribacterium methylotrophicum, Clostridium Ljungdahlii, Clostridium coskatii* and *Clostridium carboxidivorans*.

10. The method of claim 2 wherein the asymmetric membrane consists essentially of a semi-permeable skin comprising regenerated cellulose cast onto the porous polymer comprising a microporous polyethylene substrate or consists essentially of a semi-permeable skin and porous polymer both comprising polysulfone or polyethersulfone.

11. The method of claim 1 wherein the amount by which the pressure of the feed gas on the gas contacting side of the membrane is above the pressure of the fermentation liquid on the liquid contacting side of the membrane is high enough to avoid formation of a liquid layer at an interface between the microorganisms and the and the feed gas.

12. The method of claim 1 wherein the asymmetric membrane comprises a composite having a bio-layer and a hydration layer of two different materials.

13. The method of claim 1 wherein the hydration layer comprises a skin that occludes an end of the pores of the pores opposite the open end of the bio-pores.

14. The method of claim 1 wherein the pressure of the liquid on the liquid contacting side of the membrane is temporarily raised relative to the pressure on the gas contacting side of the membrane by a sufficient amount to permeate liquid into the bio-pores and onto the gas contacting side to flush microorganisms and/or biological material from the bio-pores.

15. A method for converting a feed gas containing at least one of CO or a mixture of $CO_2$ and $H_2$ to a liquid product comprising a $C_1$ to $C_6$ alcohol under anaerobic conditions, said method comprising:
    a) passing the feed gas to a gas distribution chamber;
    b) distributing the feed gas to the outer surface of a plurality of hollow fiber membranes disposed in the gas distribution chamber with each fiber defining a bio-layer comprising a porous polymer having a thickness of at least 50 μm and an outer surface providing a gas contacting side that presents a plurality of bio-pores having effective diameters of from 1 to 100 μm that open to the outer surface of the fiber and each fiber defining a hydration layer about the lumen of the fiber comprising a material that has a permeability less than permeability of the biolayer and that controls the flow of liquid to and from the biolayer;
    c) retaining an anaerobic microorganism in the bio-pores and producing the liquid product by contact of the feed gas with the microorganisms;
    d) passing a fermentation liquid having a redox potential of less than −200 mV into the lumens of the fibers and into contact with a liquid contacting side of the hydration layer to permeate a portion of the fermentation liquid from the liquid contacting side into the bio-pores and into contact with the microorganisms;
    e) withdrawing the liquid product from the microorganisms by contact of the liquid product with the fermentation liquid so that the liquid product flows with the fermentation liquid from the bio-pores to the liquid contacting surface and the feed gas and the liquid product are in co-directional flow;
    f) maintaining the feed gas on the gas contacting side of the membrane at a pressure above the pressure of the fermentation liquid on the liquid contacting side of the hydration layer by an amount that prevents the convective liquid flow from the hydration layer to the outer surface of the hollow fiber membranes;
    g) recovering a fermentation liquid containing the liquid product from the lumens of the fibers; and,
    h) separating the liquid product from the fermentation liquid to recover the liquid product.

16. The method of claim 15 wherein the hollow fibers comprise an inner skin made of a semi-permeable skin cast on the inside of the porous polymer layer, the semi-permeable skin having a thickness of less 10 μm and a nominal MWCO of less than 300 kDa and the polymer layer comprises a porous polymer having a thickness between 50 to 500 μm.

17. The method of claim 15 wherein the microorganism produces a liquid product comprising at least one of ethanol, propanol, n-butanol, and hexanol.

18. The method of claim 17 wherein the synthesis gas has an oxygen concentration of less than 1000 ppm, the bio-pores of the outer polymer layer retain a microorganism that produces ethanol and the liquid recovery conduit recovers an ethanol containing fermentation liquid from the liquid chamber.

19. The method of claim 15 wherein the microorganisms in the bio-pores comprise a mono-culture or a co-culture of at least one of *Clostridium ragsdalei, Butyribacterium methylotrophicum, Clostridium Ljungdahlii, Clostridium coskatii* and *Clostridium carboxidivorans*.

20. The method of claim 15 wherein the hollow fibers consist essentially of a semi-permeable skin comprising regenerated cellulose cast onto the porous polymer comprising a microporous polyethylene substrate or consist essentially of a semi-permeable skin and porous polymer both comprising polysulfone or polyethersulfone.

21. A method for converting a feed gas containing at least one of CO or a mixture of $CO_2$ and $H_2$ to a liquid product comprising ethanol under anaerobic conditions, said method comprising:
    a) passing the feed gas to a gas distribution chamber;
    b) distributing the feed gas the outer surface of a plurality of hollow fiber membranes disposed in the gas distribution chamber with each fiber defining a bio-layer comprising a porous polymer having a thickness of at least 50 μm and an open surface providing a gas contacting side and presenting a plurality of bio-pores having effective diameters of from 1 to 100 μm that open to the outer surface of the fiber and each fiber defining a hydration layer about the lumen of the fiber comprising a material that has a permeability less than permeability of the biolayer and that controls the flow of liquid to and from the biolayer;
    c) retaining in the bio-pores a mono-culture or a co-culture of microorganisms comprising at least one of *Clostridium ragsdalei, Butyribacterium methylotrophicum, Clostridium Ljungdahlii, Clostridium coskatii* and *Clostridium carboxidivorans* and producing ethanol by contact of the feed gas with the microorganisms;
    d) passing a fermentation liquid having a redox potential of less than −200 mV into the lumens of the fibers and into contact with a liquid contacting side of the hydration layer to permeate a portion of the fermentation liquid from the liquid contacting side into the bio-pores and into contact with the microorganisms;
    e) withdrawing the liquid product from the microorganisms by contact of the ethanol with the fermentation liquid so that the ethanol flows with the fermentation liquid from the bio-pores to the liquid contacting surface and the feed gas and the ethanol are in co-directional flow;
    f) maintaining the feed gas on the gas contacting side of the membrane at a pressure above the pressure of the fermentation liquid on the liquid contacting side of the hydration layer by an amount that prevents the convective liquid flow from the hydration layer to the open surface of the hollow fiber membranes;
    g) recovering a fermentation liquid containing the liquid product from the lumens of the fibers; and,
    h) separating the liquid product from the fermentation liquid to recover the liquid product.

* * * * *